United States Patent
Hoffmann et al.

(10) Patent No.: US 8,597,623 B2
(45) Date of Patent: Dec. 3, 2013

(54) CONDITIONING COMPOSITION FOR HAIR

(75) Inventors: Martin Hoffmann, Zwingenberg (DE); Sabine Foerster, Pfungstadt (DE)

(73) Assignee: KAO Germany GmbH, Darmstadt (DE)

( * ) Notice: Subject to any disclaimer, the term of this patent is extended or adjusted under 35 U.S.C. 154(b) by 811 days.

(21) Appl. No.: 11/559,079

(22) Filed: Nov. 13, 2006

(65) Prior Publication Data

US 2007/0110695 A1    May 17, 2007

(30) Foreign Application Priority Data

Nov. 16, 2005  (EP) ..................................... 05024989

(51) Int. Cl.
- *A61Q 5/12* (2006.01)
- *C11D 1/62* (2006.01)
- *A61K 8/02* (2006.01)

(52) U.S. Cl.
USPC ....................... 424/70.12; 424/70.28; 424/401

(58) Field of Classification Search
None
See application file for complete search history.

(56) References Cited

U.S. PATENT DOCUMENTS

| | | | | |
|---|---|---|---|---|
| 3,964,500 A | * | 6/1976 | Drakoff | 132/202 |
| 2003/0059382 A1 | * | 3/2003 | Brandt et al. | 424/59 |
| 2005/0097683 A1 | * | 5/2005 | Nocker et al. | 8/405 |

FOREIGN PATENT DOCUMENTS

| | | | |
|---|---|---|---|
| EP | 1 504 748 A | | 2/2005 |
| EP | 1504748 | * | 2/2005 |
| EP | 1 537 847 A | | 6/2005 |
| WO | WO 97/35544 | * | 10/1997 |
| WO | 99 03447 A | | 1/1999 |
| WO | 01 00141 A | | 1/2001 |

OTHER PUBLICATIONS

Sunset Hair Elements, Ingedients and what they do, wayback machine Apr. 5, 2002, pp. 1-9.*
Dow Corning 200 Product Information, Jan. 19, 1998, pp. 1-4.*
Decamethylcyclopentasiloxane @ 3Dchem.com, Mar. 2007, p. 1-2.*
Chemistry World, Advancing the Chemical Sciences, (Jan. 2005), pp. 1-4).*

* cited by examiner

*Primary Examiner* — Brian-Yong Kwon
*Assistant Examiner* — Lyndsey Beckhardt
(74) *Attorney, Agent, or Firm* — Norris McLaughlin & Marcus PA

(57) ABSTRACT

Present invention relates to aqueous conditioning composition for keratin fibers especially for hair, which provides hair long lasting, several hair washes, conditioning effect. Accordingly, present invention is a conditioning composition for hair which comprises at least one polydimethylsiloxane with a viscosity of maximum 350 mm$^2$/s at a concentration of 12.5% by weight or higher and polyquaternium 37 at a concentration of 0.2 to 5% by weight, calculated to total composition.

21 Claims, No Drawings

CONDITIONING COMPOSITION FOR HAIR

Present invention relates to aqueous conditioning composition for keratin fibres especially for hair, which provides hair long lasting, several hair washes, conditioning effect.

Rinses off conditioners have been widely used in hair care field. Silicone comprising compositions have also been known for at least last two decades. Although the state of the art has been developed quite widely, nothing or very little is done on providing conditioning compositions with long lasting conditioning effect.

The objective of the present application is providing a conditioning composition with a conditioning effect on hair, which lasts at least more than two hair washes.

It has surprisingly been found out that a conditioner composition comprising at least one polydimethylsiloxane and a cationic polymer provides such effect.

Accordingly the first object of the present invention is a conditioning composition for hair which comprises at least one polydimethylsiloxane with a viscosity of maximum 350 mm²/s at a concentration of 12.5% by weight or higher and polyquaternium 37 at a concentration of 0.2 to 5% by weight, calculated to total composition.

Second object of the invention is the use of conditioning composition for hair, which comprises polydimethylsiloxane with a viscosity of maximum 350 mm²/s at a concentration of 12.5% by weight or higher and polyquaternium 37 at a concentration of 0.2 to 5% by weight, all concentrations are calculated to total composition for conditioning hair which lasts at least 2 hair washes.

Third object of the present invention is the use of conditioning composition for hair which comprises at least one polydimethylsiloxane with a viscosity of maximum 350 mm2/s at a concentration of 12.5% by weight or higher and polyquaternium 37 at a concentration of 0.2 to 5% by weight, all concentrations are calculated to total composition, for improving hair combability, volume, elasticity and shine.

Further object of the present invention is use of conditioning composition for hair which comprises polydimethylsiloxane with a viscosity of maximum 350 mm²/s at a concentration of 12.5% by weight or higher and polyquaternium 37 at a concentration of 0.2 to 5% by weight, all concentrations are calculated to total composition, for improving hair combability, volume, elasticity and shine which lasts at least two hair washes.

Polyquaternium-37 is present in the compositions of the present invention at a concentration of 0.2 to 5%, preferably 0.2 to 4% more preferably 0.3 to 3% and most preferably 0.5 to 2% by weight, calculated to total composition.

Polydimethylsiloxanes suitable for the compositions of the present invention have a viscosity of maximum 350 mm²/s, preferably 200 mm²/s, more preferably 100 mm²/s and most preferably between 1 and 50 mm²/s.

Concentration of polymethylsiloxanes in the compositions is at least 12.5%, preferably 12.5 to 30%, more preferably 15 to 25%, most preferably 16 to 20% by weight calculated to total composition. Examples to the suitable polydimethylsiloxanes are dimethicones known with a trade name DC 200 form Dow Corning. The most preferred polydimethylsiloxanes are with a viscosity of 1 to 50 mm²/s available under the trade name DC 200 Fluid and among those polydimethylsiloxane with a viscosity of 1 mm²/s is showed excellent hair conditioning results.

In addition to the polydimethylsiloxanes, conditioner composition of the present invention comprises at least one cyclic silicone compound represented with a general formula

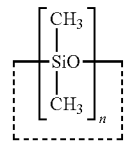

where n is a number between 3 and 7. Preferred are cyclopentasiloxanes known with the trade name for example Dow Corning 245. Concentration of cyclomethicones in the composition of present invention is in the range between 0.01 to 5%, preferably 0.02 to 4% and more preferably 0.05 to 3% and most preferably 0.1 to 2% by weight, calculated to total composition.

Further, compositions of the present invention preferably comprise at least one arylated silicone such as phenyl trimethicone commercially available under the trade names such as Dow Corning 556 and Dow Corning 558. Among the arylated silicones the most preferred one is phenyl trimethicone. Arylated silicones should be included into the compositions at a concentration of 0.1 to 10%, preferably 0.1 to 7.5%, more preferably 0.2 to 5% and most preferably 0.5 to 5% by weight, calculated to the total composition.

Additionally conditioners of the present invention may comprise cationic silicones having primary, secondary or tertiary amine or quaternary ammonium group. Suitable ones are commercially available with the known name Amodimethicone, which is available as an emulsion from Dow Corning under the trade names DC 929, DC 939 and DC 949. Concentration of cationic silicone should be in the range of 0.1 to 5%, preferably 0.1 to 4%, more preferably 0.2 to 3% by weight calculated to total composition.

One or more fatty alcohol may be incorporated into the conditioners of the present invention. Suitable ones are linear or branched, saturated or unsaturated with 10 to 24, preferably 12 to 22 carbon atoms in its alkyl chain. Nonlimiting examples are myristyl alcohol, cetyl alcohol, stearyl alcohol, palmityl alcohol, oleyl alcohol, lauryl alcohol, coconut alcohol, palm alcohol, behenyl alcohol, arachidyl alcohol and their mixtures. Preferred are myristyl alcohol, cetyl alcohol, stearyl alcohol, palmityl alcohol, oleyl alcohol, behenyl alcohol and their mixtures.

Concentration of fatty alcohol in the compositions of present invention is between 0.1 and 20%, preferably between 0.2 and 15%, more preferably 0.3 to 10% by weight calculated to total composition. The concentrations mentioned refer to the total concentration of the fatty alcohols in the case that the composition comprises more than one fatty alcohol.

Hair conditioners of present invention may comprise one or more surfactant selected form non-ionic, cationic and amphoteric ones, and/or their mixture as emulsifier, especially and preferably in the case fatty alcohol is present. Nonionic surfactants are first of all $C_{10}$-$C_{22}$-fatty alcohol ethoxylates. Especially suited $C_{10}$-$C_{22}$-fatty alcohol ethers are the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16", "Ceteareth-20".

Further non-ionic surfactants may be used in the conditioners of the present invention are compounds from the category of alkyl polyglucosides with the general formula

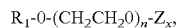

wherein $R_1$ is an alkyl group with 8 to 20, preferably 10 to 14 carbon atoms, $Z_x$ is a saccharide group with 5 to 6 carbon atoms, n stands for a number from 0 to 10, and x is a number between 1 and 5, preferably 1.1 to 2.5.

Other additionally useful surfactants are, for example, the various sorbitan esters, such as polyethylene glycol sorbitan stearic acid ester, fatty acid polyglycol ester or also mixed condensates of ethylene oxide and propylene oxide, as they are on the market, for example, under the trade name "Pluronics®".

Hydrogenated castor oil with variable ethylene glycol units is also found to be suitable non-ionic surfactant. Those are for example known from BASF under the trade name Cremophor.

Suitable cationic surfactants are particularly cetyl trimethyl ammonium chloride, steartrimonium chloride, behentrimoinium chloride, stearamidopropyl trimonuim chloride, behenamidopropylethyldimonium ethosulfate, behenamidopropyltrimonium methosulfate, cocamidopropyltrimonium chloride, cocotrimonim chloride, palmitamidopropyltrimonum chloride.

Further optional surfactant components at minor concentration may be included into the conditioners of present invention are fatty acid mono- and dialkanolamides, such as coco fatty acid monoethanolamide and myristic fatty acid monoisopropanolamide.

Conditioners of the present invention may contain amphoteric or zwitterionic surfactants. Suitable ones are in particular the various known betaines such as fatty acid amidoalkyl betaines and sulfobetaines; for example lauryl hydroxy sulfobetaine; long-chain alkyl amino acids, such as cocoaminoacetate, cocoaminopropionate and sodium cocoamphopropionate and -acetate have also proven suitable.

Conditioner compositions may contain one or more organic solvent such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylene glycol, butylenes glycol, propylene glycol, benzyl glycol, ethylene glycol monoethylether, ethylene glycol monobutyl ether, ethylene glycol monophenyl ether, 1-phenylethylalcohol, 2-phenylethylalcohol, o-methoxyphenol, and their mixture. Concentration of organic solvents in the conditioner composition can be in the range from 0.1 to 10% by weight, preferably 0.1 to 7.5% by weight, and more preferably 0.1 to 5% by weight calculated to the total composition.

Conditioner compositions of the present invention can contain additional hair conditioning agents selected from quaternary ammonium compounds, cationic polymers, additional silicone compounds, natural or synthetic oils, non-ionic conditioning agents and hair restructuring compounds.

Additionally, one or more natural oil component may be incorporated into the compositions of the present invention. Suitable are such as olive oil, almond oil, avocado oil, wheatgerm oil, ricinus oil or their mixture. Concentration of these natural oil ingredients should be 0.01 to 2.5%, preferably 0.05. to 1.5%, more preferably 0.1 to 1% by weight, calculated to total composition.

Conditioners of the present invention may comprise at least one dialkyl carbonate of the formula $R_2OC(O)OR_3$ where $R_2$ and $R_3$ are independent from each other linear or branched, saturated or unsaturated alkyl chains with 6 to 22 C atoms. Among dialkyl carbonates of the above formula, the most preferred ones are dicaprylyl carbonate known with the trade name Cetiol CC from Cognis and di(ethylhexyl) carbonate known with the trade name Tegosoft DEC from Degussa. Concentration of dialkylcarbonates in the compositions of the present invention varies between 0.1 to 20%, preferably 0.5 to 15% and more preferably 0.5 to 10% and most preferably 1 to 5% by weight, calculated to total composition.

One of the suitable conditioning agents is of quaternary ammonium compounds according to the general structure

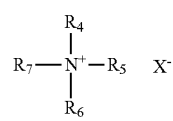

where $R_4$ is a saturated or unsaturated, branched or non-branched alkyl chain with 8-22 C atoms or $R_8CONH(CH_2)_n$ where $R_8$ is saturated or unsaturated, branched or non-branched alkyl chain with 7-21 C atoms and n has typical value of 0-4 or $R_9COO(CH_2)_n$ where $R_9$ is saturated or unsaturated, branched or non-branched alkyl chain with 7-21 C atoms and n has typical value of 0-4, and $R_5$ is a hydrogen, saturated or unsaturated, branched or non-branched alkyl chain with 1-22 C atoms or $R_8CONH(CH_2)_n$ where $R_8$ is saturated or unsaturated, branched or non-branched alkyl chain with 7-21 C atoms and n has typical value of 0-4 or $R_9COO(CH_2)_n$ where $R_9$ is saturated or unsaturated, branched or non-branched alkyl chain with 7-21 C atoms and n has typical value of 0-4, and $R_6$ and $R_7$ are independent from each other H or lower alkyl chain with 1 to 4 carbon atoms, and X is chloride, bromide or methosulfate.

Examples in addition to the ones already mentioned above as cationic surfactants are distearyldimonium chloride, dipalmitoylethylhydroxyethylmonium chloride, dioleoylethyl dimethyl ammonium methosulfate, dioleoylethyl hydroxyethylmonium methosulfate, dilinolamidopropyldimonium chloride, dioleylethyl hydroxyethylmonium chloride, dipalmitoylethyldimonium chloride.

From the above quaternary ammonium compounds disclosed with the general formula, especially to mention are those compounds known per se and are on the market, for example, under the trade names "Schercoquat®", "Dehyquart® F30" and "Tetranyl®". Use of these compounds, the so-called "esterquats", in hair care compositions is described, for example, in WO-A 93/107 48, WO-A 92/068 99 and WO-A 94/166 77, wherein, however, there is no reference made to the combinations according to the present invention and the advantageous properties thereof.

Again from the above quaternary ammonium compounds disclosed with the general formula, especially to mention are those compounds known per se and are on the market, for example, under the trade name "INCROQUAT® HO" or "OCS". These compounds are known with a general ingredient category under "amidoquat" in the cosmetic industry.

Further hair conditioning agents suitable for compositions of the present invention are those of cationic polymers best known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28. It has been found out that especially those of cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

The cationic polymers also include the quaternized products of graft polymers from organopolysiloxanes and polyethyl oxazolines described in EP-A 524 612 and EP-A 640 643.

Conditioner compositions of the present invention can optionally contain non-ionic polymers such as hydroxyethylcellulose, hydroxypropylclellulose, xanthan gum, xyloglucan, polyvinylalcohol, polyvinylpyrrolidone or their derivatives.

Anionic polymers should not be used in the conditioner compositions of the present invention as incompatibilities arose with the main thickening cationic polymer and other cationic conditioners. Typical example of those which should not be used is acrylate type of polymers know with the trade name Carbopol from Goodrich.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

$$R_{10}CO(OCH_2CH_2)_nOH$$

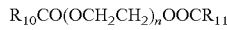
$$R_{10}CO(OCH_2CH_2)_nOOCR_{11}$$

where $R_{10}$ and $R_{11}$ are independent from each other saturated, unsaturated or branched or non-branched alkyl chain with 7 to 21 C atoms and n is typically 2-100.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

One of the known hair restructuring agents is ceramide type of compound with the general formula

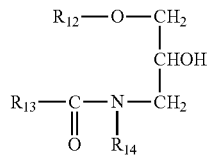

where $R_{12}$ and $R_{13}$ are independent from each other alkyl- or. alkenyl group with 10 to 22 carbon atoms, $R_{14}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Other preferred hair restructuring agents are fatty acids with 10 to 24 carbon atoms and especially with 16 to 24 carbon atoms.

Sterols, especially the phytosterols, are as well preferred hair restructuring agents as disclosed in the above mentioned german patent. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Compositions of the present invention further optionally comprise at least one ester of aliphatic linear or branched saturated or unsaturated carboxylic acid with 12 to 22 carbon atoms with a primary or secondary linear or branched saturated or unsaturated alcohol with 3 to 18 C atoms at a concentration of 0.01 to 5%, preferably 0.05. to 4%, more preferably 0.1 to 2.5% by weight, calculated to total composition. Examples include isopropyl myristate, palmitate, stearate and isostearate, oleyl oleate, isocetyl stearate, hexyl laurate, dibutyl adipate, dioctyl-adipate, myristyl myristate and oleyl erucate. The most preferred ones are isopropyl myristate, palmitate, stearate and isostearate.

The concentration of ceramide in the compositions of the present invention can be in the range of 0.01 to 2% and especially 0.01 to 1% by weight calculated to the total weight of the composition. The fatty acids may be contained at a level of 0.01 to 1% and especially 0.01 to 0.5% by weight calculated to the total weight of the composition. Phytosterol concentration of the conditioners is less than 1% and preferably less than 0.5%, more preferably 0.05 to 3% by weight calculated to the total weight of the composition. It should be noted without limiting the use of those ingredients the effect of those hair restructuring ingredients is especially elevated when used in combination with penetration enhancers.

Compositions of the present invention can comprise UV filters for protection of hair from environmental influences such as loss of elasticity, loss of hair colour (bleaching effect of sun light). The UV-absorbing substance is preferably selected from the following compounds: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher and/or 2-ethylhexyl-2-cyano-3,3-diphenyl acrylate also known as Octocrylene.

The preferred amount of the UV-absorber ranges from about 0.01% to 2.5%, more preferably from 0.05% to 1% by weight, calculated to the total composition.

The moisturising agents are selected from panthenol, polyols, such as glycerol, polyethylene glycols with molecular weight 200 to 20,000. The moisturising ingredients can be included in the conditioner compositions at a concentration range of 0.01-2.5% by weight calculated to the total composition.

Additional natural plant extracts can as well form part of the compositions of the present invention. Those are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of almond, aloe, pineapple, artichoke, arnica, avocado, valerian, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cocoanut, mango, peach, lemon, cornflower, wheat, apricot, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", $4^{th}$ Ed.

Among the natural ingredients in the form of an extract, especially preferred component of the composition according to the invention is green tea extract. This tea extract is obtained from the leaves, leaf buds and tender stems of the tea shrub, *Camellia sinensis* or *Camellia oleifera*, by aqueous or hydro-alcoholic extraction and subsequent spray-drying. In difference to black tea, green tea is a non-fermented product obtained from the *Thea sinensis* or *Thea assamica* species. An overview of the biological and pharmacological effects of green tea and the ingredients thereof can be found, e.g., in an article by A. Pistorius, "Seifen-Öle-Fette-Wachse-Journal", Volume 122., No. 7/1996, pages 468 to 471, to which reference is made. The content of green tea extract is variable in the compositions according to the invention. It preferably ranges from 0.01% to 10%, preferably 0.05% to 5% by weight, calculated to the total composition and the pulverulent extract.

Natural ingredients extracts suitable are the ones commercially available and generally include organic solvents such as propylene glycol, butylenes glycol, ethanol, isopropanol. The active matter in those extracts can vary largely, i.e. in the range of 1-30% by weight.

According to the invention, conditioning composition can comprises at least one direct acting dyestuff and is used as conditioning and colouring composition. The direct dyes referred are cationic, anionic, neutral and of plant dyes.

Suitable cationic dyestuffs are in principal those available on the market for hair colouring applications. Some examples to those are: Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51 Basic Red 76, Basic Violet 1, Basic Violet 2, Basic Violet 3, Basic Violet 10, Basic Violet 14 and Basic Yellow 57, Basic Orange 31 and Basic Yellow 87. For this purpose, special reference is made to the PCT application WO 95/15144 of Ciba-Geigy AG. All cationic dyes disclosed therein are included here by reference.

Cationic dyestuffs can be included into the compositions of the present invention at a concentration of 0.001 to 2%, preferably 0.005 to 1.5% and more preferably 0.01 to 1% by weight, calculated to total aqueous composition.

Anionic dyes may as well be used either alone or in combination with cationic direct dyes. The suitable ones are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

According to the invention, anionic dyes may be included at a concentration of 0.001 to 2%, preferably 0.005 to 1.5% and more preferably 0.01 to 1% by weight, calculated to total composition.

Additionally, the coloring compositions of the present invention may comprise neutral dyes (HC dyes), so called nitro dyes either alone or in addition to the cationic and/or anionic direct dyes. Concentration of those can typically be in the range of 0.001 to 2%, preferably 0.01 to 1.5% and more preferably 0.05 to 1% by weight calculated to total aqueous composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used in combination with cationic direct-acting dyestuffs, for example henna (red or black), alkanna root, laccaic acid, indigo, logwood powder, madder root and rhubarb powder, etc.

The pH of the conditioners of the present invention varies from 2 to 7, particularly 2 to 6.

For adjusting the pH of the said conditioner compositions, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid. Concentration of the organic and/or inorganic acids or their mixtures should be adjusted in a way that conditioner composition so obtained has a pH value between 2 to 7. Typically concentration for acids can be 0.01-5% by weight, preferably 0.01-4% by weight, more preferably 0.05-2.5% by weight calculated to the total composition. The pH of the conditioner composition can also be adjusted to the required pH by using alkaline solution such as sodium hydroxide, potassium hydroxide or their salts with those acids mentioned above in the case that at the selected acid concentration pH of the composition is lower than that of the aimed value.

Viscosity of conditioner compositions according to the present invention between 10,000 mPa·s to 60,000 mPa·s, preferably 15,000 mPa·s to 50,000 mPa·s, more preferably 20,000 to 40,000 mPa·s measured at 20° C. with Brookfield viscometer with, for example, Spindle 5 at 5 rpm. The viscosity values are read after 60 seconds from the start of the measurement. In the selection of the viscosity, special attention must be paid to the way of application and packaging to be used. It should be noted that the viscosity of the conditioners is less sensitive to temperature fluctuations. In other words, the viscosity changes observed with either decreasing or increasing temperatures is relatively small when compared to well known gel type of preparations thickened such as with hydroxyethylcellulose.

Compositions of the present invention may further comprise additional ingredients used in hair conditioning compositions as long as do not negatively influence the stability and the effect of the compositions.

Compositions of the present invention used directly on hair either after shampooing or wetting hair (without applying cleansing preparations) and rinsed off from hair with water after a processing time of maximum 30 min, preferably in the range of 1 to 20 min and more preferably in the range of 1 to 15 and most preferably 1 to 10 min. The preferred form of application is on shampooed and optionally towel dried hair.

Compositions of the present invention may also be used after mixing with a conventional conditioner at a conditioner of present invention to conventional conditioner ratio of 1:1 to 1:10, preferably 1:1 to 1:5. In such a case the compositions of the present invention boost the effect of conventional conditioners and long lasting conditioning can as well be achieved which certainly may last shorter than the same effect achieved when composition is applied without prior mixing.

The following examples should illustrate the invention but not limit it.

EXAMPLE 1

|  | % by weight |
|---|---|
| DC 200 Fluid 1 Cst | 19 |
| DC 556 | 0.5 |
| Polyqauternium-37 | 1 |
| Benzyl alcohol | 2 |
| Behentrimonium chloride | 2 |
| Ethylhexylmethoxycinnamate | 0.5 |
| Citric acid/sodium hydroxide | q.s. pH5.0 |
| Fragrance, preservative | q.s. |
| Water | to 100 |

The composition was prepared by dissolving behentrimonium chloride in water and adding the dispersion of polyquaternium 37 in DC 200 Fluid 1Cst into that and mixing until the polymer was dissolved and combined with the remaining ingredients.

The above composition was tested in a half side test with 10 female volunteers having approximately shoulder length hair. Hairdresser carried the first application and also evaluated hair status in wet and dry stages.

To this end, the volunteer's hair was washed with a conventional shampoo and the composition of example 1 above is applied to one half and the other half was applied a composition as given below as "comparative example 1". The amount of product was approximately the same, 5 g each side. After application compositions were homogenously distributed on hair and processed for 5 min and rinsed off from the hair. Hair was towel dried and evaluated by hairdresser in wet and dry stage. The results are presented in Table I.

Afterwards the volunteers were asked to wash their hair at home on the next or the day after next day (depending on volunteers washing frequency) and asked to evaluate their hair themselves. The results of the evaluation are presented in Table II.

Furthermore, the same evaluation after the first hair wash was repeated again after the second hair wash. Results are presented in Table II.

Example 1-A (Comparative)

|  | % by weight |
|---|---|
| Cetearyl alchol | 10 |
| Behentrimounium chloride | 1 |
| DC 200 Fluid 1 Cst | 1 |
| Polyquaternium-10 | 0.2 |
| Ceteareth-20 | 1 |
| Ethylhexylmethoxycinnamate | 0.5 |
| Citric acid/sodium hydroxide | q.s. pH 5.0 |
| Fragrance, preservative | q.s. |
| Water | to 100 |

TABLE I

Hair status after first application as evaluated by hairdresser

|  |  | Preferred | | |
|---|---|---|---|---|
|  | Parameter | Example 1 | Example 1-A | no preference |
| Wet | Easy combing | 7 | 1 | 2 |
|  | Smoothness | 6 | 2 | 2 |
|  | Roughness | 1 | 2 | 7 |
| Dry | Easy combing | 7 | 2 | 1 |
|  | Smoothness | 8 | 1 | 1 |
|  | Elasticity | 9 | 1 | 0 |
|  | Volume | 8 | 1 | 1 |
|  | Shine | 9 | 0 | 1 |
|  | Body | 9 | 0 | 1 |

All volunteers preferred the side treated with the composition according to the invention (Example 1).

TABLE II

Hair status after first hair wash at home evaluated by volunteers. After hair wash no conditioner was used.

|  |  | Preferred | | |
|---|---|---|---|---|
|  | Parameter | Example 1 | Example 1-A | no preference |
| Wet | Easy combing | 10 | 0 | 0 |
|  | Smoothness | 10 | 0 | 0 |
|  | Roughness | 0 | 8 | 2 |
| Dry | Easy combing | 9 | 0 | 1 |
|  | Smoothness | 9 | 0 | 1 |
|  | Elasticity | 9 | 1 | 0 |
|  | Volume | 7 | 1 | 2 |

TABLE II-continued

Hair status after first hair wash at home evaluated by volunteers.
After hair wash no conditioner was used.

| Parameter | Preferred Example 1 | Example 1-A | no preference |
|---|---|---|---|
| Shine | 9 | 0 | 1 |
| Body | 9 | 0 | 1 |

All volunteers preferred the side treated with the composition according to the invention (Example 1).

TABLE III

Hair status after second hair wash at home evaluated by volunteers.
After hair wash no conditioner was used.

| | Parameter | Preferred Example 1 | Example 1-A | no preference |
|---|---|---|---|---|
| Wet | Easy combing | 8 | 0 | 2 |
| | Smoothness | 8 | 0 | 2 |
| | Roughness | 1 | 8 | 1 |
| Dry | Easy combing | 7 | 0 | 3 |
| | Smoothness | 7 | 1 | 2 |
| | Elasticity | 8 | 1 | 2 |
| | Volume | 7 | 1 | 2 |
| | Shine | 8 | 0 | 2 |
| | Body | 7 | 1 | 2 |

9 volunteers preferred the side treated with the composition according to the invention (Example 1) and 1 did not prefer any side.

From third wash on the volunteers were allowed to use their conventional conditioner only on the side they feel it needed. Number of hair washes where no additional conditioner used was asked to the volunteers. The results are in Table III.

TABLE III

Additional conditioner was used after (Xth) wash

| | Example 1 | Example 1-A |
|---|---|---|
| 3$^{rd}$ wash | 1 | 10 |
| 4$^{th}$ wash | 3 | — |
| 5$^{th}$ wash | 4 | — |
| 6$^{th}$ wash | 2 | — |

From the above results, it is clear that Example 1 gives hair long lasting conditioning effect. The effect lasts on average 4.7 hair washes.

Similar results were obtained with the following examples.

Example 2

| | % by weight |
|---|---|
| DC 200 Fluid 1 Cst | 23 |
| Cyclomethicone | 1.5 |
| Polyquaternium-37 | 1.2 |
| Phenoxyethanol | 2.5 |
| Cetrimonium chloride | 1.5 |

-continued

| | % by weight |
|---|---|
| Benzophenone-3 | 0.3 |
| Cetyl PG-hydroxyethylpalmitamide | 0.1 |
| Cetearyl alcohol | 1 |
| Citric acid/sodium hydroxide | q.s. pH5.0 |
| Fragrance, preservative | q.s. |
| Water | to 100 |

Example 3

| | % by weight |
|---|---|
| DC 200 Fluid 1 Cst | 23 |
| Cyclomethicone | 1.5 |
| Polyqauternium-37 | 1.2 |
| Phenoxyethanol | 2.5 |
| Amodimethicone[1] | 0.2 |
| Cetrimonium chloride | 1.5 |
| Benzophenone-3 | 0.3 |
| Cetyl PG-hydroxyethylpalmitamide | 0.1 |
| Cetearyl alcohol | 1 |
| Basic red 51 | 0.1 |
| Citric acid/sodium hydroxide | q.s. pH 5.0 |
| Fragrance, preservative | q.s. |
| Water | to 100 |

[1]DC 949 from Dow Corning, the concentration relate to amidimethicone active matter.

The above conditioner is a colour enhancing conditioner gives dark blond hair excellent red touch.

Example 4

| | % by weight |
|---|---|
| DC 200 Fluid 1 Cst | 23 |
| Cyclomethicone | 1.5 |
| Polyquaternium-37 | 1.2 |
| Phenoxyethanol | 2.5 |
| Cetrimonium chloride | 1.5 |
| Panthenol | 0.5 |
| Benzophenone-3 | 0.3 |
| Isopropylpalmitate | 0.1 |
| Cetearyl alcohol | 1 |
| Basic red 51 | 0.1 |
| Citric acid/sodium hydroxide | q.s. pH 5.0 |
| Fragrance, preservative | q.s. |
| Water | to 100 |

The invention claimed is:

1. A conditioning composition for hair comprising polydimethylsiloxane with a viscosity in the range of 1 to 50 mm$^2$/s at a concentration of 16 to 30% by weight, polyquaternium 37 at a concentration of 0.2 to 5% by weight, calculated to total composition, and one or more fatty alcohols.

2. The composition of claim 1, additionally comprising at least one cyclic silicone compound according to formula

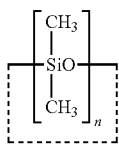

where n is a number between 3 and 7.

3. The composition of claim 1, additionally comprising at least one arylated silicone.

4. The composition of claim 1, comprising at least one surfactant selected from nonionic, cationic, amphoteric ones or their mixtures.

5. The composition of claim 1, additionally comprising at least one organic solvent.

6. The composition of claim 1, additionally comprising at least one quaternary ammonium compound of the chemical structure

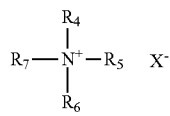

where $R_4$ is a saturated or unsaturated, branched or non-branched alkyl chain with 8-22 C atoms, and $R_5$ is a hydrogen, saturated or unsaturated, branched or non-branched alkyl chain with 1-22 C atoms and $R_6$ and $R_7$ are independent from each other H or lower alkyl chain with 1 to 4 carbon atoms, and X is chloride, bromide or methosulfate.

7. The composition of claim 1, additionally comprising one or more cationic polymer.

8. The composition of claim 1, additionally comprising additionally ceramide type of compound according to general formula

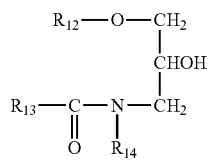

where $R_{12}$ and $R_{13}$ are independent from each other alkyl- or alkenyl group with 10 to 22 carbon atoms and $R_{14}$ is alkyl or hydroxyl alkyl with 1 to 4 carbon atoms group.

9. The composition of claim 1, comprising at least one UV filter.

10. The composition of claim 1, comprising at least one ester of aliphatic linear or branched saturated or unsaturated carboxylic acid with 12 to 22 carbon atoms with a primary or secondary linear or branched saturated or unsaturated alcohol with 3 to 18 C atoms at a concentration of 0.01 to 5% calculated to total composition.

11. The composition of claim 1, comprising at least one direct dye.

12. The composition of claim 1, comprising a pH between 2 and 7.

13. A process for conditioning hair characterized in that a composition according to claim 1 is applied onto shampooed or wetted hair, and processed for 1 to 30 min and rinsed off.

14. A process for conditioning hair characterized in that a composition according to claim 1 is mixed with a conditioner comprising at least one hair conditioning compound and applied onto shampooed or wetted hair, and processed for 1 to 30 min and rinsed off.

15. The composition according to claim 1 wherein the Polyquaternium-37 is present at a concentration of between 0.2% to 4% by weight.

16. The composition according to claim 15 wherein the Polyquaternium-37 is present at a concentration of between 0.3% to 3% by weight.

17. The composition according to claim 1 wherein the concentration of fatty alcohol in the composition is between 0.1 to 20% by weight.

18. The composition according to claim 17 wherein the concentration of fatty alcohol in the composition is between 0.3 to 10% by weight.

19. The composition according to claim 1 wherein the concentration of polydimethylsiloxane is between 19-23% by weight.

20. The composition according to claim 19, wherein the concentration of polydimethylsiloxane is about 19% by weight.

21. The composition according to claim 19, wherein the concentration of polydimethylsiloxane is about 23% by weight.

* * * * *